United States Patent [19]

Hammonds et al.

[11] Patent Number: 4,857,637

[45] Date of Patent: Aug. 15, 1989

[54] METHODS AND COMPOSITIONS FOR IMMUNOLOGICALLY MODULATING GROWTH HORMONE RECEPTOR ACTIVITY

[75] Inventors: R. Glenn Hammonds, San Francisco; David W. Leung, Foster; David W. Martin, Jr., San Francisco; Steven A. Spencer; William I. Wood, both of San Mateo, all of Calif.

[73] Assignee: Genentech, Inc., South San Francisco, Calif.

[21] Appl. No.: 61,942

[22] Filed: Jun. 12, 1987

Related U.S. Application Data

[63] Continuation-in-part of Ser. No. 861,236, May 7, 1986, which is a continuation of Ser. No. 737,302, May 22, 1985, abandoned.

[51] Int. Cl.$^4$ .................... C12P 21/00; C12P 19/34; C12N 15/00; C07H 15/12
[52] U.S. Cl. .................................. 530/403; 530/402; 530/810; 424/88; 430/519; 430/543
[58] Field of Search ...................... 424/85, 86, 87, 88; 530/402, 403, 810; 436/519, 543

[56] References Cited

U.S. PATENT DOCUMENTS 4,761,371 8/1988 Bell et al. .............................. 435/68

FOREIGN PATENT DOCUMENTS 0142345 5/1985 European Pat. Off. .

OTHER PUBLICATIONS

Heinemann et al. "Modulation of acetylcholine receptor by antibody against the receptor", Proc. Natl. Acad. Sci. USA, vol. 74, No. 7, 3090–3094, Jul. 1977.
Couraud et al., "Antibodies Raised Against β-Adrenergic Receptors Stimulate Adenylate Cyclase", Biochem Biophys Res Comm., vol. 99, No. 4, 1295–1302, Apr. 1981.
Farid, Nadir R. "Immunology Letters", 9:191–199, (Apr. 1985).

Kelsoe, G. et al., "Immunological Review", 52:75–88, (1980).
Noseworthy, J. N. et al., "J. of Immunology", 131(5):2533–2538, (Nov. 1983).
Flier, J. S. et al., "Science", 190:63–65, (Oct. 1975).
Kennedy, R. C. et al., "Science", 22:853–855, (Aug. 1983).
Marx, J. L., "Science", 228:162–165, (Apr. 1985).
Venter, J. C. et al., "Federation Proceedings", 43(10):2532–2539, (Jul. 1984).
Couraud, P. O. et al., "J. Exp. Med.", 157:1369–1378, (May 1983).
McNamara, M. K. et al., "Science", 226:1325–1326, (Dec. 1984).
Sacks, D. L. et al., "J. Exp. Med.", 155:1108–1119, (Apr. 1982).
Schreiber, A. B. et al., "Proc. Natl. Acad. Sci. USA", 77(12):7385–7389, (Dec. 1980).
Ng, D. S. et al., "European J. Pharmacology", 102:187–190 (1984).
Ibbotson, K. J. et al., "Endocrinology", 116(1):469–471, (1985), (Given to Postal Service on Dec. 20, 1984).
Djiane, J. et al., "Proc. Natl. Acad. Sci. USA", 78(12):7445–7448, (Dec. 1981).
Cadman, H. F. et al., "FEBS Letters", 137(1):149–152, (Jan. 1982).
Leiber et al., "Proc. Natl. Acad. Sci. USA", 81:4331–4334, (Jul. 1984).
Jacobs, S. et al., "Science", 200:1282–1283, (Jun. 1978).

(List continued on next page.)

Primary Examiner—Morton Foelak
Assistant Examiner—Nathan M. Nutter
Attorney, Agent, or Firm—Max D. Hensley

[57] ABSTRACT

The activity of growth-associated receptors is modulated in vivo in a controlled and reproducible fashion by immunizing animals against target growth-associated receptors. This is accomplished by the use of immunogens predetermined to induce primarily agonist or antagonist responses. The immunogens include anti-ligand antibodies and receptor derivatives.

10 Claims, 6 Drawing Sheets

OTHER PUBLICATIONS

Fernandez-Pol, J. A. et al., "J. Biol. Chem.", 260(8):5003–5011, (Apr. 1985).
Kahn, C. R. et al., "J. Clin. Invest.", 60:1094–1106, (Nov. 1977).
Surowy, T. K. et al., "Mol. Immunol.", 21(5):345–352, (1984).
Barnard, R. "Biochem. J.", 231:459–468, (1985).
Duplock, R. C. et al., Abstract from Mtg. of The Endocrine Society of Australia, Adelade, 1985.
Valente, W. A. et al., "New Eng. J. Med.", 309(17):1028–1034, (Oct. 1983).
Valente, W. A. et al., "Proc. Natl. Acad. Sci. USA", 79:6680–6684, (Nov. 1982).
Kris et al., Cell 40:619–625, (1985).

```
      -144                                                                                     TTAG
      -140 TATAATGTTA TCTGGTTGCA TATATGGCTA AGTGAAAAGA AAATTGAAGA GTTTCTTGAT ACAAAGCCTG

-70  GAGGGAGCTA CACGTTCAAA AATCCAACTT CTATATCAGG AACATCTGCT GGACTATTGG TCCTACAGGT

1 ATGGATCTCT GGCAGCTGCT GTTGACCGTG GCACTAGCAG GGTCAAGTGA TGCTTTTTCT GGGAGTGAGG
       -18 MetAspLeuT rpGlnLeuLe uLeuThrVal AlaLeuAlaG lySerSerAs pAlaPheSer GlySerGluAla

71 CCACACCAGC TACCCTTGGC AGAGCATCCG AGAGTGTGCA AAGAGTTCAT CCAGGCCTGG GGACAAATTC
         7    ThrProAl aThrLeuGly ArgAlaSerG luSerValGl nArgValHis ProGlyLeuG lyThrAsnSer

141 TTCTGGGAAG CCCAAATTCA CCAAGTGCCG TTCACCTGAA CTAGAGACTT TTTCATGCCA CTGGACAGAT
        30   SerGlyLys ProLysPheT hrLysCysAr gSerProGlu LeuGluThrP heSerCysHi sTrpThrAsp

211 GGGGTTCATC ATGGTTTAAA GAGCCCAGGA TCTGTGCAGC TGTTCTATAT TAGGAGGAAC ACTCAAGAAT
        53 GlyValHisH isGlyLeuLy sSerProGly SerValGlnL euPheTyrIl eArgArgAsn ThrGlnGluTrp

281 GGACTCAAGA ATGGAAAGAA TGCCCTGACT ATGTTTCTGC TGGGAGAAC AGCTGTTACT TTAATTCATC
        77    ThrGlnGl uTrpLysGlu CysProAspT yrValSerAl aGlyGluAsn SerCysTyrP heAsnSerSer

351 CTATACCTCC ATTTGGATCC CCTACTGTAT CAAGCTAACT AACAATGGTG GTATGGTGGA TCAAAAGTGT
       100   TyrThrSer IleTrpIleP roTyrCysIl eLysLeuThr AsnAsnGlyG lyMetValAs pGlnLysCys

421 TTCTCTGTTG AGGAAATAGT GCAACCAGAT CCACCCATTG GCCTAACTG GACTTTACTG AATGTTAGCT
       123 PheSerValG luGluIleVa lGlnProAsp ProProIleG lyLeuAsnTr pThrLeuLeu AsnValSerLeu

491 TAACCGGGAT TCATGCAGAT ATTCAAGTGC GATGGGAACC ACCACCCAAT GCAGATGTTC AGAAGGGATG
       147    ThrGlyIl eHisAlaAsp IleGlnValA rgTrpGluPr oProProAsn AlaAspValG lnLysGlyTrp

561 GATAGTCTTG GAGTATGAAC TTCAATACAA AGAAGTCAAT GAAACTCAAT GGAAAATGAT GGACCCTGTA
       170   IleValLeu GluTyrGluL euGlnTyrLy sGluValAsn GluThrGlnT rpLysMetMe tAspProVal

631 TTGTCGACAT CAGTTCCTGT GTACTCGTTA AGACTGGACA AAGAATATGA AGTGCGTGTG AGATCCAGAC
       193 LeuSerThrS erValProVa lTyrSerLeu ArgLeuAspL ysGluTyrGl uValArgVal ArgSerArgGln

701 AGCGAAGCTC TGAAAAATAT GGCGAGTTCA GTGAGGTGCT CTATGTAACC CTTCCTCAAA TGAGCCCATT
       217   ArgSerSe rGluLysTyr GlyGluPheS erGluValLe uTyrValThr LeuProGlnM etSerProPhe ncoI
       771 CACATGTGAA GAAGATTTCC GGTTTCCATG GTTCTTAATT ATTATCTTTG GAATATTTGG ACTAACAGTG
       240   ThrCysGlu GluAspPheA rgPheProTr pPheLeuIle IleIlePheG lyIlePheGl yLeuThrVal 841 ATGCTATTCG TATTCATATT TTCTAAACAG CAAAGGATTA AGATGCTGAT TCTGCCCCCA GTTCCAGTTC
       263 MetLeuPheV alPheIlePh eSerLysGln GlnArgIleL ysMetLeuIl eLeuProPro ValProValPro claI
       911 CAAAGATTAA AGGAATCGAT CCAGATCTCC TCAAGGAAGG AAAGTTAGAG GAGGTGAACA CAATCTTAGC
       287   LysIleLy sGlyIleAsp ProAspLeuL euLysGluGl yLysLeuGlu GluValAsnT hrIleLeuAla ecoRI                          ecoRI                     claI
       981 CATTCAAGAT AGCTATAAGC CTGAATTCTA CAATGATGAC TCTTGGGTTG AATTCATCGA GCTAGACATC
       310   IleGlnAsp SerTyrLysP roGluPheTy rAsnAspAsp SerTrpValG luPheIleGl uLeuAspIle 1051 GATGACCCTG ATGAAAAGAC TGAGGGATCA GACACAGACC GACTTCTAAG CAACAGCCAT CAGAAATCAC
       333 AspAspProA spGluLysTh rGluGlySer AspThrAspA rgLeuLeuSe rAsnSerHis GlnLysSerLeu 1121 TTAGCGTCCT TGCAGCAAAG GATGACGACT CTGGACGAAC CAGCTGTTAC GAACCTGACA TCCTGGAGAA
       357   SerValLe uAlaAlaLys AspAspAspS erGlyArgTh rSerCysTyr GluProAspI leLeuGluAsn 1191 TGATTTCAAT GCCAGTGACG GGTGCGACGG GAACTCGGAG GTTGCTCAGC CTCAAAGGTT AAAAGGGGAA
       380   AspPheAsn AlaSerAspG lyCysAspGl yAsnSerGlu ValAlaGlnP roGlnArgLe uLysGlyGlu 1261 GCAGATCTCT TGTGCCTTGA CCAGAAGAAT CAAAATAACT CACCTTACCA TGATGTTTCT CCTGCTGCTC
       403 AlaAspLeuL euCysLeuAs pGlnLysAsn GlnAsnAsnS erProTyrHi sAspValSer ProAlaAlaGln
```

FIG.1A

```
1331 AGCAGCCTGA GGTCGTCCTA GCAGAGGAAG ACAAACCGCG ACCACTTCTT ACTGGTGAGA TTGAATCCAC
 427    GlnProGl uValValLeu AlaGluGluA spLysProAr gProLeuLeu ThrGlyGluI leGluSerTh

1401 TCTTCAGGCT GCACCTTCTC AGCTCAGCAA TCCAAATTCA CTGGCAAACA TCGACTTTTA CGCCCAGGTT
 450    LeuGlnAla AlaProSerG lnLeuSerAs nProAsnSer LeuAlaAsnI leAspPheTy rAlaGlnVal
                                                                              ecoRI
1471 AGTGACATTA CGCCGGCAGG GAGTGTGGTC CTTTCCCCAG GCCAGAAGAA CAAGGCAGGG AATTCTCAGT
 473    SerAspIleT hrProAlaGl ySerValVal LeuSerProG lyGlnLysAs nLysAlaGly AsnSerGlnC 1541 GTGATGCGCA TCCAGAAGTC GTCTCACTCT GCCAGACAAA CTTCATCATG GACAACGCCA ACTTCTGTGA
 497    AspAlaHi sProGluVal ValSerLeuC ysGlnThrAs nPheIleMet AspAsnAlaT yrPheCysGl
                                                                                hindIII
1611 AGCAGATGCC AAAAAGTGTA TCGCTGTGGC CCCTCATGTC GACGTCAAT CACGTGTCGA GCCAAGCTTT
 520    AlaAspAla LysLysCysI leAlaValAl aProHisVal AspValGluS erArgValGl uProSerPhe 1681 AACCAGGAGG ACATTTACAT CACCACAGAA AGCCTTACCA CTACTGCCGA GAGGTCTGGG ACAGCAGAAG
 543    AsnGlnGluA spIleTyrIl eThrThrGlu SerLeuThrT hrThrAlaGl uArgSerGly ThrAlaGluA 1751 ACGCCCCAGG TTCTGAGATG CCTGTCCCAG ACTATACCTC CATTCATTTA GTACAATCTC CACAAGGCCT
 567    AlaProGl ySerGluMet ProValProA spTyrThrSe rIleHisLeu ValGlnSerP roGlnGlyLe 1821 TGTACTCAAT GCAGCCACCT TGCCCTTGCC TGACAAAGAG TTTCTCTCAT CGTGTGGCTA CGTGAGCACA
 590    ValLeuAsn AlaAlaThrL euProLeuPr oAspLysGlu PheLeuSerS erCysGlyTy rValSerThr 1891 GACCAACTGA ACAAAATCTT GCCATAGCCT TCTTTGATG TCCAAGAGCT TTGTATCTAA TGGCAAAGAA
 613    AspGlnLeuA snLysIleLe uProAM*

1961 TTGGCTGTGG CATGAATGCT TAAACCAAAC CAGTGTAAGG GGAATGGAAG AGTAGGTTGT GGATTCTAAA

2031 TGCCTTCTCT GAAATTTGAA ACAGGATATT AAAAAGAAAA AACTAAGAGG AATGCTTAAT CAGATAGATA

2101 TTCCTGTTGT GAACTGTAAA TATTTTAAAG AATTGTCTCA AATACTGTTT AGTGGCAGTA ATTGTCTTCT

2171 TGTGGGTGTT AATTTTGTGA TACTAAACAT TGAATGGCTA TGTTTTAAT GTATAGTAGA ATCATGCTTT
                                pstI
2241 TTGAAAAAGC GAAAAATCAG GTGGCTTCTG CAGTTCAGGA GAACTGAATG AAAATCATAG CACAGACTAA
                                                                              ecoRV
2311 TTTTTTTCTT CTTAATTAAT TGGGAGCTAA CACTATAGGT AAGAAGGCAA AAATAGTTTG GATATCTAAA 2381 ACACTTATTT TGACATAAAC TTGATAAAGA TATTTTTAAG AAGTTAAATT TCAAGCATGG CTATTTTATA 2451 TCACCCTATA CACTGTGTAC TGTAGTTCAA GAAGATTCAT CTACAGAATG TAGCAACTAC AGTCTCAAGC

2521 TGGTTTGATG CTTTTCATCA GTGCACCTAA AGAAACACA CACAAGTGTT TTTTTACAAG GTCCTTTTTG

2591 TACCTTCCAA AACTCATTGA TTCTAAAATG ATTGTAAAAA TTTGCATATC GGAACATACT TATTTTATCT

2661 GAATTTCTAA TCAAATATTT GTTAAATTTA GAAAATTTTT AATATTTGC ACAAATAAAC TTACATAAAT

2731 CAAAAACCAA ACAACACAAA ACTTTTCTTT ACCAAATCTT GGTTCGTGCC AGACAGCTGC ATGCGAAGAG

2801 AAGTAGAAAT CATTGCTGGT TCACGTTGAC CACAAGACTT AAGTTCTACA GTGGCATGTG GACTGATTTA
                               pstI
2871 GTGCATGCAG ACCATGAGAG GTAAGCTCTA TAACCTCTGC AGTAAAATCT CTTCAAATAT AACTCGATTT 2941 TATTTCATAT TTACCGAAGA GAGGAAGTTG AAGCAGGTCA AATGAAGCTA ACTGGGTAAA GGAACAGAAA 3011 TAGGTTTTGT TTCACAGCCT TTACCCAGAC ACATACATAG TCAGTATTCA TGGCAACAAG AAATAAAAGA 3081 AACAAGGTTT TCAATCCCCA CAGATAACTC AGAGTTACTT AAACTAGGAG CAGAAACTTT CTCACCAAAA 3151 TTTTTATAAG ATTTAGTTAA ACAGTAAAAG AAGATGTTTC ATCATTTTTA TTTCCCTCCA AGTAGTCCAG
```

FIG.1B

```
3221 CCTCAAAGCA GGTAGTCAGA AAAAAGAAA GGGACTTGA GTAATTTGTA GATTTTCCAA TTCCTTAATA
3291 ACCTAAGTAT CATTTTAGA AGCATAGGGA TAGTTCCCAA AAGGATTATG AAAATGAGAA TACTTAACCA
3361 TTTTAAGAAT TTTTTATATT CTTTTTAAAG TTAGCATTCA CTTAAATAGT ATTTGCCATT TAGCTCAGAC
              hindIII
3431 CCCTTTAGAA AGCAAGCTTT ATGATTGGTA AGTTTTAATT CCTTCTCTCA TTCAAGAAAG ATGGTGGAAA
3501 GCTAGACCTG GGTGTTTAAA GTTTACCGTG ATACTTTGTA GTAGATGTTT AATAGATTTT CTGCTACCTT
3571 GCTGCTATGG TCTTCTCCAA GAGCTACATA ATTTAGTTTC ATATACAATA TCATCACAGT AGAACCTAAT
3641 TCAACTTAAA ACTATGTGTT TGGAAGAACT ATCTTACCAT TTCACAATAG GCTAACAACA TTTCTATAGC
3711 CAAAAATAGC TAAATACCTC AATCAGTCTC AGAATGTCAT TTTGGTACTT TGCTGGCCAC ACAAGCCATT
                                     pstI
3781 ATTCACTAGT ATGACTAGTT GTGTCCTGCA GTTTATATTT AACTTTCTTT ATGTCTGTGG ATTTTTTCC
3851 TTCAAAGTTT AATAAATTTA TTTTTCTTGAA AAAAA
```

FIG.1C

```
-43                              CCG CGCTCTCTGA TCAGAGGCGA AGCTCGGAGG TCCTACAGGT

1 ATGGATCTCT GGCAGCTGCT GTTGACCTTG GCACTGGCAG GATCAAGTGA TGCTTTTTCT GGAAGTGAGG
 -18 MetAspLeuT rpGlnLeuLe uLeuThrLeu AlaLeuAlaG lySerSerAs pAlaPheSer GlySerGluAla

71 CCACAGCAGC TATCCTTAGC AGAGCACCCT GGAGTCTGCA AAGTGTTAAT CCAGGCCTAA AGACAAATTC
   7    ThrAlaAl aIleLeuSer ArgAlaProT rpSerLeuGl nSerValAsn ProGlyLeuL ysThrAsnSer

141 TTCTAAGGAG CCTAAATTCA CCAAGTGCCG TTCACCTGAG CGAGAGACTT TTTCATGCCA CTGGACAGAT
  30 SerLysGlu  ProLysPheT hrLysCysAr gSerProGlu ArgGluThrP heSerCysHi sTrpThrAsp

211 GAGGTTCATC ATGGTACAAA GAACCTAGGA CCCATACAGC TGTTCTATAC CAGAAGGAAC ACTCAAGAAT
  53 GluValHisH isGlyThrLy sAsnLeuGly ProIleGlnL euPheTyrTh rArgArgAsn ThrGlnGluTrp

281 GGACTCAAGA ATGGAAAGAA TGCCCTGATT ATGTTTCTGC TGGGGAAAAC AGCTGTTACT TTAATTCATC
  77    ThrGlnGl uTrpLysGlu CysProAspT yrValSerAl aGlyGluAsn SerCysTyrP heAsnSerSer

351 GTTTACCTCC ATCTGGATAC CTTATTGTAT CAAGCTAACT AGCAATGGTG GTACAGTGGA TGAAAGTGT
 100  PheThrSer IleTrpIleP roTyrCysIl eLysLeuThr SerAsnGlyG lyThrValAs pGluLysCys

421 TTCTCTGTTG ATGAAATAGT GCAACCAGAT CCACCCATTG CCCTCAACTG GACTTTACTG AACGTCAGTT
 123 PheSerValA spGluIleVa lGlnProAsp ProProIleA laLeuAsnTr pThrLeuLeu AsnValSerLeu ecoRV
 491 TAACTGGGAT TCATGCAGAT ATCCAAGTGA GATGGGAAGC ACCACGCAAT GCAGATATTC AGAAAGGATG
 147    ThrGlyIl eHisAlaAsp IleGlnValA rgTrpGluAl aProArgAsn AlaAspIleG lnLysGlyTrp 561 GATGGTTCTG GAGTATGAAC TTCAATACAA AGAAGTAAAT GAAACTAAAT GGAAAATGAT GGACCCTATA
 170· MetValLeu GluTyrGluL euGlnTyrLy sGluValAsn GluThrLysT rpLysMetMe tAspProIle 631 TTGACAACAT CAGTTCCAGT GTACTCATTG AAAGTGGATA AGGAATATGA AGTGCGTGTG AGATCCAAAC
 193 LeuThrThrS erValProVa lTyrSerLeu LysValAspL ysGluTyrGl uValArgVal ArgSerLysGln 701 AACGAAACTC TGGAAATTAT GGCGAGTTCA GTGAGGTGCT CTATGTAACA CTTCCTCAGA TGAGCCAATT
 217    ArgAsnSe rGlyAsnTyr GlyGluPheS erGluValLe uTyrValThr LeuProGlnM etSerGlnPhe ncoI
 771 TACATGTGAA GAAGATTTCT ACTTTCCATG GCTCTTAATT ATTATCTTTG GAATATTTGG GCTAACAGTG
 240 ThrCysGlu  GluAspPheT yrPheProTr pLeuLeuIle IleIlePheG lyIlePheGl yLeuThrVal 841 ATGCTATTTG TATTCTTATT TTCTAAACAG CAAAGGATTA AAATGCTGAT TCTGCCCCCA GTTCCAGTTC
 263 MetLeuPheV alPheLeuPh eSerLysGln GlnArgIleL ysMetLeuIl eLeuProPro ValProValPro claI
 911 CAAAGATTAA AGGAATCGAT CCAGATCTCC TCAAGGAAGG AAAATTAGAG GAGGTGAACA CAATCTTAGC
 287    LysIleLy sGlyIleAsp ProAspLeuL euLysGluGl yLysLeuGlu GluValAsnT hrIleLeuAla ecoRI
 981 CATTCATGAT AGCTATAAAC CCGAATTCCA CAGTGATGAC TCTTGGGTTG AATTTATTGA GCTAGATATT
 310 IleHisAsp  SerTyrLysP roGluPheHi sSerAspAsp SerTrpValG luPheIleGl uLeuAspIle 1051 GATGAGCCAG ATGAAAAGAC TGAGGAATCA GACACAGACA GACTTCTAAG CAGTGACCAT GAGAAATCAC
 333 AspGluProA spGluLysTh rGluGluSer AspThrAspA rgLeuLeuSe rSerAspHis GluLysSerHis 1121 ATAGTAACCT AGGGGTGAAG GATGGCGACT CTGGACGTAC CAGCTGTTGT GAACCTGACA TTCTGGAGAC
 357    SerAsnLe uGlyValLys AspGlyAspS erGlyArgTh rSerCysCys GluProAspI leLeuGluThr kpnI
1191 TGATTTCAAT GCCAATGACA TACATGAGGG TACCTCAGAG GTTGCTCAGC ACAGAGGTT AAAAGGGGAA
 380 AspPheAsn  AlaAsnAspI leHisGluGl yThrSerGlu ValAlaGlnP roGlnArgLe uLysGlyGlu 1261 GCAGATCTCT TATGCCTTGA CCAGAAGAAT CAAAATAACT CACCTTATCA TGATGCTTGC CCTGCTACTC
 403 AlaAspLeuL euCysLeuAs pGlnLysAsn GlnAsnAsnS erProTyrHi sAspAlaCys ProAlaThrGln 1331 AGCAGCCCAG TGTTATCCAA GCAGAGAAAA ACAAACCACA ACCACTTCCT ACTGAAGGAG CTGAGTCAAC
 427    GlnProSe rValIleGln AlaGluLysA snLysProGl nProLeuPro ThrGluGlyA laGluSerThr
```

FIG.2A

```
1401 TCACCAAGCT GCCCATATTC AGCTAAGCAA TCCAAGTTCA CTGTCAAACA TCGACTTTTA TGCCCAGGTG
 450  HisGlnAla  AlaHisIleG  lnLeuSerAs  nProSerSer  LeuSerAsnI  leAspPheTy  rAlaGlnVal
                                                      smaI
1471 AGCGACATTA CACCAGCAGG TAGTGTGGTC CTTTCCCCGG GCCAAAAGAA TAAGGCAGGG ATGTCCCAAT
 473  SerAspIleT hrProAlaGl  ySerValVal  LeuSerProG lyGlnLysAs nLysAlaGly  MetSerGlnCys 1541 GTGACATGCA CCCGGAAATG GTCTCACTCT GCCAAGAAAA CTTCCTTATG GACAATGCCT ACTTCTGTGA
 497   AspMetHi  sProGluMet ValSerLeuC ysGlnGluAs nPheLeuMet AspAsnAlaT yrPheCysGlu
                                                                              hindIII
1611 GGCAGATGCC AAAAAGTGCA TCCCTGTGGC TCCTCACATC AAGGTTGAAT CACACATACA GCCAAGCTTA
 520  AlaAspAla  LysLysCysI leProValAl aProHisIle LysValGluS erHisIleGl nProSerLeu 1681 AACCAAGAGG ACATTTACAT CACCACAGAA AGCCTTACCA CTGCTGCTGG GAGGCCTGGG ACAGGAGAAC
 543  AsnGlnGluA spIleTyrIl eThrThrGlu  SerLeuThrT hrAlaAlaGl yArgProGly  ThrGlyGluHis 1751 ATGTTCCAGG TTCTGAGATG CCTGTCCCAG ACTATACCTC CATTCATATA GTACAGTCCC CACAGGGCCT
 567   ValProGl ySerGluMet  ProValProA spTyrThrSe rIleHisIle ValGlnSerP roGlnGlyLeu 1821 CATACTCAAT GCGACTGCCT TGCCCTTGCC TGACAAAGAG TTTCTCTCAT CATGTGGCTA TGTGAGCACA
 590  IleLeuAsn AlaThrAlaL  euProLeuPr oAspLysGlu PheLeuSerS erCysGlyTy  rValSerThr 1891 GACCAACTGA ACAAAATCAT GCCTTAGCCT TTCTTTGGTT TCCCAAGAGC TACGTATTTA ATAGCAAAGA
 613  AspGlnLeuA snLysIleMe tProAM*

1961 ATTGACTGGG GCAATAACGT TTAAGCCAAA ACAATGTTTA AACCTTTTTT GGGGGAGTGA CAGGATGGGG

2031 TATGGATTCT AAAATGCCTT TTCCCAAAAT GTTGAAATAT GATGTTAAAA AATAAGAAG AATGCTTAAT

2101 CAGATAGATA TTCCTATTGT GCAATGTAAA TATTTTAAAG AATTGTGTCA GACTGTTTAG TAGCAGTGAT

2171 TGTCTTAATA TTGTGGGTGT TAATTTTTGA TACTAAGCAT TGAATGGCTA TGTTTTTAAT GTATAGTAAA

2241 TCACGCTTTT TGAAAAAGCG AAAAAATCAG GTGGCTTTTG CGGTTCAGGA AAATTGAATG CAAACCATAG

2311 CACAGGCTAA TTTTTTGTTG TTTCTTAAAT AAGAAACTTT TTTATTTAAA AAACTAAAAA CTAGAGGTGA

2381 GAAATTTAAA CTATAAGCAA GAAGGCAAAA ATAGTTTGGA TATGTAAAAC ATTTACTTTG ACATAAAGTT
                                                                              pstI
2451 GATAAAGATT TTTTAATAAT TTAGACTTCA AGCATGGCTA TTTTATATTA CACTACACAC TGTGTACTGC 2521 AGTTGGTATG ACCCCTCTAA GGAGTGTAGC AACTACAGTC TAAAGCTGGT TTAATGTTTT GGCCAATGCA 2591 CCTAAAGAAA AACAAACTCG TTTTTTACAA AGCCCTTTTA TACCTCCCCA GACTCCTTCA ACAATTCTAA 2661 AATGATTGTA GTAATCTGCA TTATTGGAAT ATAATTGTTT TATCTGAATT TTTAAACAAG TATTTGTTAA

2731 TTTAGAAAAC TTTAAAGCGT TTGCACAGAT CAACTTACCA GGCACCAAAA GAAGTAAAAG CAAAAAGAA

2801 AACCTTTCTT CACCAAATCT TGGTTGATGC CAAAAAAAAA TACATGCTAA GAGAAGTAGA AATCATAGCT

2871 GGTTCACACT GACCAAGATA CTTAAGTGCT GCAATTGCAC GCGGAGTGAG TTTTTTAGTG CGTGCAGATG
                      pstI
2941 GTGAGAGATA AGATCTATAG CCTCTGCAGC GGAATCTGTT CACACCCAAC TTGGTTTTGC TACATAATTA

3011 TCCAGGAAGG GAATAAGGTA CAAGAAGCAT TTGTAAGTT GAAGCAAATC GAATGAAATT AACTGGGTAA

3081 TGAAACAAAG AGTTCAAGAA ATAAGTTTTT GTTCACAGC CTATAACCAG ACACATACTC ATTTTTCATG

3151 ATAATGAACA GAACATAGAC AGAAGAAACA AGGTTTTCAG TCCCCACAGA TAACTGAAAA TTATTTAAAC

3221 CGCTAAAAGA AACTTTCTTT CTCACTAAAT CTTTTATAGG ATTTATTTAA AATAGCAAAA GAAGAAGTTT
```

FIG.2B

```
3291 CATCATTTTT TACTTCCTCT CTGAGTGGAC TGGCCTCAAA GCAAGCATTC AGAAGAAAAA GAAGCAACCT
3361 CAGTAATTTA GAAATCATTT TGCAATCCCT TAATATCCTA AACATCATTC ATTTTTGTTG TTGTTGTTGT
3431 TGTTGAGACA GAGTCTCGCT CTGTCGCCAG GCTAGAGTGC GGTGGCGCGA TCTTGACTCA CTGCAATCTC
3501 CACCTCCCAC AGGTTCAGGC GATTCCCGTG CCTCAGCCTC CTGAGTAGCT GGGACTACAG GCACGCACCA
                                                                xhoI
3571 CCATGCCAGG CTAATTTTTT TGTATTTTAG CAGAGACGGG GTTTCACCAT GTTGGCCAGG ATGGTCTCGA
3641 GTCTCCTGAC CTCGTGATCC ACCCGACTCG GCCTCCCAAA GTGCTGGGAT TACAGGTGTA AGCCACCGTG
                                            ecoRV
3711 CCCAGCCCTA AACATCATTC TTGAGAGCAT TGGGATATCT CCTGAAAAGG TTTATGAAAA AGAAGAATCT
                                         hindIII
                                                 hindIII
3781 CATCTCAGTG AAGAATACTT CTCATTTTTT AAAAAAGCTT AAAACTTTGA AGTTAGCTTT AACTTAAATA
3851 GTATTTCCCA TTTATCGCAG ACCTTTTTA GGAAGCAAGC TTAATGGCTG ATAATTTTAA ATTCTCTCTC
3921 TTGCAGGAAG GACTATGAAA AGCTAGAATT GAGTGTTTAA AGTTCAACAT GTTATTTGTA ATAGATGTTT
3991 GATAGATTTT CTGCTACTTT GCTGCTATGG TTTTCTCCAA GAGCTACATA ATTTAGTTTC ATATAAAGTA
4061 TCATCAGTGT AGAACCTAAT TCAATTCAAA GCTGTGTGTT TGGAAGACTA TCTTACTATT TCACAACAGC
4131 CTGACAACAT TTCTATAGCC AAAAATAGCT AAATACCTCA ATCAGTCTCA GAATGTCATT TTGGTACTTT
4201 GGTGGCCACA TAAGCCATTA TTCACTAGTA TGACTAGTTG TGTCTGGCAG TTTATATTTA ACTCTCTTTA
4271 TGTCTGTGGA TTTTTTCCTT CAAAGTTTAA TAAATTTATT TTCTTTGGATT CCTGATAATG TGCTTCTGTT
4341 ATCAAACACC AACATAAAAA TGATCTAAAC CAAAAAAAAA AAAAAAAAA AAA
```

FIG.2C

METHODS AND COMPOSITIONS FOR IMMUNOLOGICALLY MODULATING GROWTH HORMONE RECEPTOR ACTIVITY

This is a continuation-in-part of U.S. Ser. No. 06/861,236 filed May 7, 1986 which in turn is a continuation of U.S. Ser. No. 06/737,302 filed May 22, 1985 and now abandoned.

This invention is concerned with controlling the activity of cell surface receptors in a population of animals. In particular it relates to the field of immunologically modulating the activity of receptors having a role in cell proliferation and growth.

Receptors are proteins found associated with cell surfaces that specifically bind proteins or small molecules in the extracellular environment (henceforth referred to as "ligands") and which, upon binding such ligands, exert an effect on the metabolic or morphologic character of the cell. Receptors that effect growth are the focus of this invention, but this invention is by no means limited to such receptors.

Such receptors henceforth are referred to as receptors for growth-associated ligands, or growth-associated receptors for short. They include receptors for ligands heretofore identified as growth factors and growth hormones. Examples are the growth factor receptors for growth hormones such as human, bovine, porcine or bovine growth hormones and growth factors such as epidermal growth factor, insulin-line growth factor and transforming growth factors alpha and beta (henceforth abbreviated as EGF, IGF and TGF-$\alpha$ and TGF-$\beta$). Other growth-associated receptors have been and are continuing to be identified concomitant with the development of knowledge of the mechanisms underlying cell growth and proliferation. Insulin, thyroid stimulating hormone and neurotransmitter (e.g. acetylcholine or catecholamine) receptors are not included within the scope of growth associated receptors.

Antibodies to cell surface receptors have been made by immunizing animals against the intact receptors per se or against fragments thereof linked to proteins to form immunogenic conjugates. These antibodies exert a variety of effects on cells bearing the receptors. For example, antibodies to insulin receptors purified from rat liver membranes were found to have insulin-like activity, even though the antibody bound to the insulin receptor at a site different from that to which insulin binds (S. Jacobs et al., 1983 "Science", 200: 1283). A similar phenomenon occurs with certain antibodies to acetylcholine and catecholamine receptors (S. Heinemann et al., 1977, "P.N.A.S. USA" 74: 3090; P.-O. Couraud et al., 1981, "Biochem. Biophys. Res. Commun." 99: 1295). Several monoclonal antibodies from mice immunized with cells containing large numbers of EGF receptors have been reported which inhibit EGF binding to EGF receptors but which nonetheless mimic the biological effects of EGF (A. Schreiber et al., 1981, "P.N.A.S. USA" 78(12): 7535).

Other antibodies generated by immunization with cell surface receptors have the opposite effect: They block both the binding of ligand to the receptor as well as the biological activity of the receptor. This has been the case for antibodies raised against the prolactin receptor (R.P.C. Shiv et al., 1976, "Science" 207: 1362), the cardiac muscle $\beta$-adrenergic receptor (S. Wrenn et al., 1978, "J. Biol. Chem." 254: 6577) and the EGF receptor (H. Haigler et al., 1980, "Biochem. Biophys. Acta" 598: 314).

Immunization against receptors therefore produces antibodies which bind the receptor and in doing so may either mimic the normal ligand or inhibit the activity of the normal ligand without stimulating any receptor biological activity. These results are believed to stem from the inherent variability in polyclonal antibody response to receptor immunogens on both an intra or interspecies basis.

Schreiber et al. (op cit) chose to resolve this variability in anti-receptor response by immunizing mice with the EGF receptor and thereafter identifying monoclonal cell lines obtained from the immunized mice that exhibited agonistic activity, i.e., that stimulated receptor activity. While such antibodies would find use in a passive immunization program to stimulate the EGF receptor, they are inadequate for therapeutic or growth modulatory functions requiring continuous modulation over a long period of time. For example, passive immunization in order to induce extensive growth of epidermal tissue of the induction of gigantism in livestock would require the frequent administration of monoclonal antibodies over a long period of time, on the order of months or years. In this case, immuno-modulation of receptor activity offers no advantages over simple administration of the ligand hormone or factor per se, and in fact could be disadvantageous since non-murine monoclonal antibodies are not available in any significant scale and murine antibodies can be expected to be immunogenic in other economically important species; continuous administration of large amounts of foreign protein is well known to create a risk of "serum sickness" and kidney failure.

It therefore would be desirable to provide methods and compositions for inducing in animals an autoimmune response to a target growth-associated receptor in such animal, but one which if it occurs at all is highly specific to a receptor epitope selected for its ability to bind antibody in a way that will elicit either an agonistic or antagonistic response as is appropriate to the therapeutic objectives sought in modulating the receptor activity.

SUMMARY

According to the invention herein the foregoing objective is accomplished by immunizing an animal against a selected cell surface receptor of the animal by vaccinating the animal with an immunogen selected from the group of (a) antibodies capable of binding the ligand for the receptor or (b) a receptor derivative, said antibodies or receptor derivative having beem predetermined to raise polyclonal antisera in a plurality of animals which consistently affect the receptor as either substantially a ligand agonist or antagonist. Either of these embodiments results in raising the autoimmune, predetermined response in the immunized animal which is directed against targeted sites in the receptor to consistently produce the desired therapy. In contrast to the past, where autoimmune responses have been associated with diseases, this invention induces such responses to achieve desired objectives.

Novel compositions provided herein include conjugates of an immunogenic substance with a derivative or a polypeptide fragment of a receptor wherein the fragment comprises a receptor epitope predetermined to raise an antibody response in a plurality of animals which is consistently and substantially either ligand agonist or antagonist. The derivative or fragment is selected so that it will not raise a polyclonal response upon immunization that contains a substantial degree of both ligand agonist and antagonist effect. Instead, fragments or derivatives are chosen so as to be substantially devoid of immunologically-recognized epitopes which will induce a polyclonal response in which antibodies are present that have the undesired activity, thereby foreclosing the auto-immune generation of antibodies that act adversely to the therapeutic objectives.

Other novel compositions include conjugates of an immunogenic protein with a fragment of an anti-ligand antibody which includes the variable region of the antibody.

In a particular embodiment the method herein comprises stimulating the growth of an animal or predetermined tissues, glands or organs thereof, by immunizing the animal against an immunogen selected from the group of (a) antibodies capable of binding an animal growth hormone or (b) a polypeptide fragment of an animal growth hormone receptor, which fragment comprises a receptor epitope predetermined to bind antibody as a growth hormone agonist. This method enables the continuous growth of target tissues without the need to frequently administer growth hormone, thereby obtaining the advantages heretofore available only upon continuous administration of growth hormone, e.g. enhanced milk production and weight gain, but by a single immunization treatment followed by infrequent booster immunizations as required.

BRIEF DESCRIPTION OF THE DRAWINGS

FIGS. 1 and 2 are the nucleotide and amino acid sequences for the rabbit and human growth hormone receptors, respectively.

DETAILED DESCRIPTION

Receptors for growth-associated ligands are defined as cell surface proteins having extracellular domains or regions that bind to a ligand in such a way as to induce cell growth or proliferation. Growth-associated ligands generally are polypeptides (including proteins) that bind to receptors to induce such cell growth or proliferation. Such ligands are considered hormones when they act to regulate the growth of tissues during development or maturation of an animal. Ordinarily such hormones act to stimulate growth during a certain stage of development or maturation.

The distinction between growth hormones and growth factors is ill-defined. For purposes only of this application, growth hormones are to be considered a species of growth factors. The principal characteristic of both species of growth-associated ligands is their mitogenic activity in vitro and, ordinarily, in vivo. Growth factors, like growth hormones, induce in vitro cell proliferation or other morphological changes associated with cell proliferation. For example, EGF initially stimulates nutrient uptake, enhances phosphorylation of endogenous membrane proteins and induces changes in cell structure and cytoskeletal organization. Delayed responses to EGF include the activation of cytoplasmic enzymes and the stimulation of DNA synthesis. EGF receptors are found in the cell membranes of epidermal cells such as corneal tissue, and extremely dense populations in the cell membranes of some malignant cells.

Animal growth hormone is secreted by the pituitary. In its mature form it consists of about 191 amino acids and has a molecular weight of about 21,500. Animal growth hormones have been fully described in the literature. Growth hormone from human, bovine, chicken, porcine and other sources have been identified and sequenced. Growth hormone plays an important role in the growth of long bones during development, but it also has direct or indirect stimulatory activity towards certain mature tissues, e.g. it is known to stimulate milk production in cattle.

The induced polyclonal response consistently affects the target receptor when greater than about 60 percent (and preferably 80 percent of a test population of animals responds in the desired manner (i.e. evidences agonist or antagonist net activity). The test population is a plurality of animals, generally about from 10 to 100, of the same strain or genotype.

One objective of this invention is to provide methods and compositions to generate autoimmune antibodies in vivo that will act as agonists of growth-associated ligands, but without formation of substantial antagonist antibodies in the target population. Here the autoimmune antibody stimulates or induces the receptor to act in the same or substantially the same manner qualitative as the native ligand, although the quantitative efficacy may be greater or lesser than the ligand.

On the other hand, since growth-associated ligands also have been implicated in tumorigenesis, it may be therapeutically desirable to inhibit or suppress the activity of the receptor for the ligand. EGF receptors in high cell surface density characterize the human A-431 epidermoid carcinoma cell line (R. Fabricant et al., 1977, "P.N.A.S. USA" 74: 565–569). In a recent study 4 out of 10 human glioblastomas were found to have overexpressed cell surface EGF receptors (T. Libermann et al., 1984, "Cancer Res." 44: 753–760). In this embodiment the objective of this invention will be to generate autoimmune antibodies in vivo that act as antagonists of growth-associated ligands.

Other therapies in which autoimmune ligand agonist or antagonist activity is desired will be apparent to the ordinary artisan as further knowledge of disease processes becomes known, particularly in the area of degenerative or developmentally related conditions. In particular, osteoporosis is a debilitating disease in which bone is resorbed faster than it is deposited. The etiology of this disease is complex, but ultimately it is manifest as an imbalance in the activity of osteoclastic cells as compared to osteoblasts. One therapeutic approach will be to immunize a patient having osteoporosis with an immunogenic conjugate of a fragment of the vitamin D receptor predetermined to induce agonist antibodies.

While reference is made herein to "autoimmune", it should be understood that this means simply the raising of antibodies of any class in an animal that will immunologically recognize a self antigen. It does not mean that the immunogen used must be the same as or derived from the animal to be immunized.

The embodiments herein require immunization of animals against anti-ligand antibodies, growth factor receptor derivatives or, optionally, intact growth factor receptors. In all cases the immunizations are to be conducted in accordance with standard methods for raising antibodies against proteins or polypeptides. In general, poorly immunogenic proteins are rendered more immunogenic by the use of adjuvants, e.g. Freunds, and/or by conjugating the target protein or polypeptide to immunogens, either by the use of covalent or noncovalent bonds. Covalent conjugates are prepared by linking the target to immunogens such as keyhole limpet haemocyanin, soybean trypsin inhibitor, bovine thyroglobulin, bovine serum albumin and the like, or by synthesizing fusion proteins of the target with an immunogen such as a bacterial or viral protein. Obviously, the immunogenic polypeptide will be chosen from the perspective of the species which is to be immunized, i.e. the polypeptide should be heterolgous or foreign to the animal species being immunized. Also, the immunogenic polypeptide is suitably a microbial polypeptide, e.g. beta-galatosidase, fMet-Leu-Phe, trpE, beta-lactamase and the like, which is linked to the target protein by chemical crosslinking or by expression as amino or carboxyl-terminal fusions in recombinant cell culture.

When covalent conjugates are made by chemical crosslinking, one can employ various cross-linking agents, including those described below in Table 1.

TABLE 1

| Peptidyl or Protein Reactive Group(s) | Coupling Agent | Peptidyl or Protein Reactive Group(s) |
|---|---|---|
| —NH$_2$ | glutaraldehyde | —NH$_2$; —OH |
| —NH$_2$ | succinic anhydride | —NH$_2$ |
| O<br>—C—NH$_2$ | H$_2$N—NH$_2$; HNO$_2$ | —NH$_2$; —SH; —OH |
| —NH$_2$; —SH | R'N=C=NR | —COOH |
| —COOH | SOCl$_2$ | —COOH |
| —COOH | N—hydroxy-succinimide | —NH$_2$ |
| —SH | M—maleimidobenzyl sulfosuccinimide ester | —SH |

Other cross-linking agents heretofore employed in conjugating proteins to solids, e.g. those used in the preparation of affinity adsorption columns or immobilized immunoassay, are known to the ordinary artisan and useful for preparing immunogens.

The immunogen also is linked to the target protein or polypeptide by noncovalent means known per se in the art, including but not limited to formation of precipitates, e.g. with alum, by inclusion in liposomes, or by physical entrapment in aggregates, e.g. immunogenic protein such as bovine serum albumin crosslinked with glutaraldehyde.

The immunogenicity-conferring agent generally is a polypeptide, as described above. However, it also is suitably a solid material, e.g. an implantable nitrocellulose filter which, in concert with the target protein, induces a strong immune response. This response is accentuated by including chemotactic polypeptides, e.g. fMet-Leu-Phe, in the implantable matrix so as to attract macrophages.

It should be understood that the target polypeptides are often capable on their own of eliciting an immune response. However, this response is improved by the use of immuno potentiators, i.e. adjuvants, particularly where the target is poor immunogenic. This is typically the case with haptenic or lower molecular weight receptor or ligand fragments (about from 5 to 20 residues) and anti-idiotypic antibodies from or closely related to the species being immunized.

The objectives of this invention are accomplished by the use of two embodiments. In a first embodiment the invention comprises immunizing an animal with an antibody capable of binding the ligand for the receptor. This embodiment is advantageous because it does not require the identification, characterization or other knowledge of the receptor with which the ligand ordinarily interacts. This method generally uses as immunogen either the anti-ligand antibody or its variable region, i.e., liquid binding fragment of the anti-ligand antibody, either of which also may be bound to an immunogenic protein. The immunogen antibody need not be soluble. It may be present on monoclonal cell surfaces, embedded in liposomal membranes or bound in insoluble immunogenic aggregates with other proteins. This embodiment is particularly adapted to stimulate, i.e., act as an agonist for receptors. However, this embodiment also is useful in producing antibodies that act as antagonists towards receptors. This is accomplished by raising an anti-ligand antibody against an antagonist ligand rather than either an agonist ligand or the natural ligand for the receptor.

If the immunogen antibody is from the same species as that which is being immunized, the resulting immune response is characterized as anti-idiotypic. This is because the immunized animal recognizes the constant regions of the immunogen antibody as self but recognizes the variable region (which binds to ligand) as foreign. The immunogen anti-ligand antibody generally is from a different species than the species that is being immunized, while the ligand used to raise the immunogen antibody may be from the same species in which it is desired to raise the anti-ligand antibody response.

The polyclonal response resulting from immunization with a non-anti-idiotypic anti-ligand antibody is directed at all epitopes of the immunogen antibody, including its ligand binding epitopes in the variable region. These ligand binding epitopes are the regions which are immunologically homologous with the receptor ligand-binding site. Thus antibodies raised against these epitopes will bind to cell surface receptors. Antibodies raised against antibodies that bind epitopes elsewhere on the ligand can be expected to not bind to the receptor and therefore will likely but not necessarily be immunologically neutral in the receptor therapy provided herein. The effect of the anti-antiligand antibody on the receptor must be experimentally confirmed. The character of the immune response in the animal species or strain that is to be obtained with any given immunogen, i.e. agonist, antagonist or without effect on receptor, is determined readily by in vivo or in vitro screening methods provided elsewhere herein. Having made this determination, and since the activity of the immune response as agonistic or antagonistic is relatively constant within a given animal strain for a selected immunogen antibody, the immunogen is used with confidence in therapy. The confidence level is greater where it is desired to immunize domesticated animals, e.g. for weight gain or milk yield improvements, because such animals tend to be inbred and will exhibit a greater constancy of response to a given immunogen.

More specifically, the first embodiment of this invention requires as a first step that an animal of species 1 be immunized against the growth associated ligand. This is a routine procedure well known in the art. For example, the ligand (which need not be purified) is completed with a carrier and combined with an adjuvant such as complete Freund's or precipitated in a complex such as with alum and thereafter injected subcutaneously at multiple sites, or intraperitoneally. Since the immunogen antibodies for use herein are preferably monoclonal antibodies, the immunogenic ligand compositions should be used to immunize mice, for which methods are readily available to produce monoclonal antibodies. If the initial anti-ligand antibody titers are inadequate, two weeks after the initial injection the animal is boosted with the immunogenic ligand in incomplete Freund's or other adjuvant.

The ligand is from any species (including, potentially species 1) having the ability to interact with the receptor of the animal to be immunized (species 2). Preferably the ligand is obtained or derived from species 2.

Serum titers of anti-ligand conveniently are measured by a sandwich assay. For example, if mice are immunized then the sandwich assay will use immobilized ligand and labelled polyclonal rabbit anti-mouse immunoglobulin (or vice versa) in conventional fashion. When the anti-ligand titer has reached a plateau, B cells from the immunized mice are fused with myeloma cells or otherwise immortalized using conventional methods, e.g. EB virus infection. Immortalized immune cells are distributed into microtiter plates and the antibody produced by each clone assayed for anti-ligand activity following the above procedure.

As a further preferred embellishment, clones producing (or antisera containing) anti-ligand antibody are further selected or purified for antibody having ligand neutralizing activity. This embellishment may be used where the ligand receptor or cells bioaffected by the ligand binding have been identified. This embellishment is not critical but is often useful in enhancing and resolving the immune response to the immunogen antibody. Suitable antibody is identified by its ability upon preincubation with labelled ligand to inhibit the binding of labelled ligand to receptor or to inhibit bioactivity of unlabelled ligand. Such assays are known per se. Such identified antibodies are termed ligand-neutralizing antibodies.

The immunogen anti-ligand antibody, once identified, is recovered from immunized animals or monoclonal antibody cell culture. The antibody is preferably partially purified from plasma or culture in the fashion of routine immunoglobulin preparative techniques, e.g. using salting out, affinity chromatography on immobilized ligand columns, polyethylene glycol fractionation, or solvent precipitations. Suitable methods, e.g. the Cohn fractionation techniques, are well known. Concentrated solutions of the immunogen antibody, typically in glycine buffers or saline, are sterile filtered through membranes and, if desired, lyophilized for long-term storage.

It generally is preferred that the immunogen antibody be selected from the IgG immunoglobulin class. A large proportion of anti-ligand antibody will be IgG, and IgG is more stable than IgM. However, other antibody classes such as IgM, IgD or IgA may be employed as immunogen antibodies.

Also within the scope of immunogen antibody are fragments thereof, so long as such fragments contain at least the variable region in its proper conformation. A typical fragment is the Fab fragment obtained in conventional fashion by enzyme digestion of intact antibody.

As noted above, it is not necessary for the immunogen antibody to have been raised only against the ligand of the species which is to immunized by the anti-ligand antibody. For example, an animal growth hormone from species 1 is used for immunization of species 2, but the resulting immunogen antibody from species 2 is useful not only with species 1 but with other phylogenetically related species. More specifically, murine monoclonal anti-human growth hormone antibodies are useful for the immunization of cattle against the bovine growth hormone receptor.

Routine experimentation will be necessary to determine the optimal immunogen antibody and immunization program for each anti-receptor therapy. Typically, a matrix experiment will be conducted in which the character of the immunogen antibody is varied, together with the immunization program, to identify the most effective method. The efficacy of the matrix experiment is monitored by in vivo or in vitro assays, depending upon the desired therapy. For example, cattle immunized against murine anti-bovine growth hormone receptor will be monitored for changes in milk output. Alternatively, known in vitro biological assays are employed to assess any growth hormone activity by antibodies raised by test immunogens.

While the objective of the embodiments of this invention is to identify and obtain receptor immunogens that will only induce antibodies in vivo having either substantially agonist activity or substantially antagonist activity, but not both, it is obvious that the polyclonal immune response frequently will result in some B-cell clones being induced in a minor subpopulation of immunized recipients that synthesize antibodies not having the desired activity. On balance, however, immunogens will be selected that produce the desired response in the target recipient population as a whole. This is particularly so, as noted above, with inbred domesticated animals such as dairy cattle where the allelic variation in the major histo compatibility complex is minimal.

In the first embodiment described above, agonist or antagonist activity is induced substantially free of antagonist or agonist activity, respectively, by virtue of the preselection of receptor epitope by raising antibodies against only the ligand, where the receptor binding site is the major relevant epitope. The second embodiment of this invention makes this selection by using as immunogens derivatives of the target receptors that, upon vaccination of the target population, induce substantially only the predetermined agonist or antagonist activity. The derivatives accomplish this by masking or deleting undesired epitopes, i.e. epitopes that stimulate the undesired immune response. The receptors concerned are cell surface receptors because these are accessible to auto-immune antibodies, whereas, as a practical matter in vivo, intracellular receptors are not.

The amino acid sequences for certain growth-associated receptors, e.g., for the EGF receptor, are known (A. Ullrich et al., 1984, "Nature" 309: 418–425). Other growth factor receptors, e.g., the insulin-like growth factor-1 receptor, have been partially purified or otherwise identified. Once a receptor has been purified and, preferably, its amino acid sequence determined then this embodiment can be used. Growth factor receptors commonly comprise extracellular, transmembrane and cytoplasmic domains. The cytoplasmic domains of these receptors may carry nucleotide triphosphate binding sites, protein phosphokinase sites and, in some cases, autophosphorylation sites. However, the portion of growth-associated receptors which is of interest herein is the extracellular region because this region is accessible to antibodies under in vivo conditions, unlike the intracellular or cytoplasmic domains.

The knowledge of the extracellular amino acid sequence of growth-associated receptors, and particularly of those sequences which represent or flank the ligand binding site, is helpful in selecting receptor derivatives for use as immunogens in screening assays, and particularly in selecting fragment polypeptides for recombinant or in vitro synthesis. These polypeptide subunits or fragments of the entire receptor are rendered immunogenic and used to auto-immunize animals against their endogenous receptor to generate either agonist or antagonist antibodies, depending upon the polypeptide employed and the manner in which it is rendered immunogenic. Preferably, the best candidate polypeptides are identified in vitro by prescreening them for binding to agonist or antagonist antibodies that had been previously obtained by immunization with an immunogen comprising the intact receptor. Thus, under this approach the receptor epitopes that stimulate the generation of undesired polyclonal antibodies are not exposed to the animal recipient at all. However, other methods for masking the undesired receptor epitopes also are useful. For example, the ligand or an active fragment thereof is allowed to bind to receptor and then is conjugated to the receptor binding site by photoactivation, as described below.

This immunogen will be effective in generating antibodies that bind to epitopes which flank the ligand-binding site. These antibodies are good candidates for antagonist activity. Other conventional protein derivatization techniques can be used to mask critical amino acid residues. For example, if the receptor binding site contains a lysine residue that is critical for ligand binding but no other lysine residue flanks the binding site or is important in maintaining receptor conformation, then the receptor is reacted with an N-hydroxysuccinimide derivation in order to substitute the lysine amino side chain.

The preferred method used to prescreen appropriate receptor derivative immunogens comprises, first, obtaining antibodies that exert either an antagonist or agonist activity on the target receptors and, second, selecting those immunogens that bind to test or screening antibodies having the desired activity. Immunogens useful for the production of agonist antibodies should bind to agonist antibodies, and vice versa for antagonist antibodies. Some such antibodies are already known, for example see A. Schreiber et al., op cit., for an EGF agonist monoclonal antibody. While goats, rabbits, horses, cattle or mice are all suitable candidates for receptor immunization, mice preferably are immunized as it is convenient to prepare monoclonal antibodies from immunized mice.

Immunizing animals against the intact or substantially intact target receptor gives rise to a polyclonal population of antibodies having agonist, antagonist and/or no detectable biological effect or activity. If the intact, native target receptor is syngeneic to the animal to be immunized, the receptor should be conjugated to a foreign carrier so as to be recognized as foreign in the animal to be immunized, as is generally described above. For example, if the DNA encoding a receptor is cloned and an expression system has been developed, e.g. as in the case of the EGF receptor, the receptor is expressed as a mutant in which DNA encoding immunogenic sequences have been inserted or substituted for native receptor DNA. In the case of the EGF receptor, DNA encoding a substantial amino terminal region of a bacterial protein such as TrpE or beta-galactosidase is inserted in place of the EGF receptor secretion signal sequence.

After an animal has been immunized, antisera or supernatants from hybridoma culture are screened for the desired agonist or antagonist antibody. In the case of monoclonal antibodies this selection is facilitated by microtiter plate screening methods now known in the art wherein thousands of clones can be rapidly screened for the desired activity by immune competition or by bioassays. Competitive-type methods facilitate the selection of antibodies that can compete with ligand for binding to its receptor. This group of ligand-competitive antibodies constitutes an enriched selection group for agonist and antagonist antibodies. Such competitively binding antibodies are either binding so as to (1) inhibit ligand binding without exerting a ligand-like effect in vivo, as will occur with antibodies that bind epitopes in the steric vicinity of the ligand binding site or which bind the site improperly, or (2) inhibit ligand binding with a ligand-like biological effect in vivo, as will occur when the antibodies bind the ligand binding site, and bind it in such a fashion as to mimic ligand activity. This is not to say that antibodies which do not compete with ligand for receptor binding always fail to exhibit agonist or antagonist activity. However, ligand-competitive antibodies are the most likely source for such antibodies. Note that these antibodies are unlike the immunogen antibodies described in the first embodiment because immunogen antibodies are anti-ligand antibodies while the antibodies of this embodiment are anti-receptor antibodies. The anti-ligand antibodies are therapeutic compositions in their own right, while the anti-receptor, ligand-competitive antibodies are used in methods described below to identify candidate receptor polypeptide immunogens.

A typical screening method for competitively-binding antibody is described as follows: Monoclonal cell culture supernatants or immunoglobulins from immune plasma to be tested are coated on the wells of microtiter plates by methods known per se for coating antisera on plastic surfaces. The sensitivity of the assay will be enhanced if the wells are precoated with antisera raised against the immunoglobulins of the species supplying the candidate screening antibody, e.g. rabbit anti-mouse IgG. Antibody which has not bound to the walls of the microtiter wells is aspirated and the wells optionally washed with buffer at a pH of about 6–8. Thereafter, separate dilutions of receptor and labelled ligand are added to each well and the distribution of labelled ligand between the insoluble and soluble phases determined. This is accomplished by adding receptor and ligand simultaneously or sequentially, incubating, aspirating and, if desired, washing. If the antibody binds to the receptor in competition with ligand, the ligand will prevent receptor binding to the candidate antibody in proportion to the amount of labelled ligand present. Thus, if increasing concentrations of ligand have no substantial effect on the amount of antibody bound to the solid phase one can conclude that the antibody and ligand are not competing for the same receptor site.

For large scale analysis it is more convenient to coat the wells with receptor, whether cell membrane-bound or solubilized prior to coating, and measure the competition of labelled ligand with candidate antibody for a limited number of receptor sites.

Generally, the ligand is labelled with iodine 125 or 131 by methods known per se, but other known labels such as fluorescent molecules, rare earth chelates or enzymes are suitable. Labelled ligands such as bovine growth hormone are known.

Other methods for detecting receptor binding of the antibody at the active site will be apparent to the ordinary artisan. For example, changes in the fluorescence spectrum of fluorescent-labelled ligand which are induced by receptor binding can be followed in solution in the presence of candidate antibody dilutions. Or it is possible to use an EMIT type immunoassay, where the ligand is labelled with an enzyme; the EMIT assays are to be used with small molecular weight ligands, e.g. on the order of 300 to 3000 Daltons.

A more direct screening method, which is used after or in place of assays for competitive-binding activity in non-living systems, is to obtain tissue explants or to establish cells in tissue culture that are known to be activated or affected in a detectable fashion by a normal ligand, the activity of which it is desired to agonize or antagonize. To identify agonists the screening is conducted by incubating the antibodies with cells or cell lines which are known to express target cell surface receptors, and thereafter measuring for growth promoting activity such as the induction of mitosis or other metabolic or morphologic changes ordinarily induced by the ligand. Antagonistic antibodies are identified by the same assay except that growth repressive activity is selected which is not overcome by increasing concentrations of ligand in the incubation. For example, animal cell cultures are known that are capable of anchorage-independent growth in agar in the presence of epidermal growth factor (EGF). In order to determine whether an EGF receptor fragment or anti-EGF antibody is capable of inducing an antibody that will act as an EGF antagonist, one need only raise test antibody in suitable animals and use the antibody to pretreat the cell cultures before exposure to EGF. If the antibody reduces the number of anchorage-independent colonies growing in agar culture one can conclude that the receptor fragment or anti-EGF antibody are candidates for therapeutic use as EGF antagonists. Growth affecting activity on other cell lines may be measured by numerous known assays such as incorporation of macromolecular precursors (e.g. Tdr or Leu) or by cellular proliferation.

Suitable cells or cell lines for use in bioactivity assays already are known. For example, the A-431 cell line mentioned above expresses the EGF receptor. Placental cells express the IGF-1 receptor. Other suitable cells or cell lines are identified by selecting cell lines showing strong immunofluorescence upon coating with fluorescein-labelled anti-receptor antibody. Here, any anti-receptor antibody can be used because detection of gross receptor population is the sole objective. Such antibodies are known, e.g. see M. Waterfield et al., "J. Cell Biochem." 210: 149-161 (1982).

Agonistic or antagonistic antibodies have been observed to naturally occur in vivo, for example the insulin antagonist antibody reported by J. Flier et al., op cit. Such antibodies are also suitable for use as anti-receptor derivative antibodies when available.

The identified or preexisting agonistic or antagonistic antibodies then are used to identify cross-reactive receptor derivatives that are therefore candidate immunogens for raising such antibodies for therapeutic purposes. This is accomplished by preparing a library of candidate polypeptide immunogens and determining whether or not they are bound by the detection antibodies. If bound by an antagonistic antibody, the polypeptide immunogen is suitable for raising antibodies to inhibit the growth of cells dependent upon the receptor in question. Immunogens for agonist antibodies are identified by their ability to bind to agonist antibodies. The preferred immunogens will only bind to the antibody representing the desired effect. For example, this means than an immunogen capable of binding to an agonist antibody should be screened with the antagonist antibody to ensure that the immunogen also is not potentially capable of raising antagonist antibodies.

Candidate immunogenic receptor fragments generally are made by one of three methods. They may be synthesized by in vitro organic chemical methods, by enzymatic or nonenzymatic cleavage of receptor or by recombinant expression of portions of the DNA encoding the receptor. Of the three methods, organic synthesis is preferred. However, the other two methods offer certain advantages.

Receptor is enzymatically digested with one or more endoproteolytic enzymes (exopeptidases may be used for tailoring fragments obtained in previous endoproteolytic digestion). Such enzymes are widely available from microbial or mammalian sources. Many of these enzymes heretofore have been used to fragment proteins as an initial step in amino acid sequencing. Examples include crypsin, lysine-C protease, chymotrypsin and carboxy-peptidase. Preferably the enzymes chosen will have known cleavage sites to enable more accurate control of fragment generation.

Receptors also are hydrolyzed using non-enzymatic cleavage agents such as cyanogen bromide, which cleaves proteins at methionine residues, and acetic acid, which cleaves at aspartate residues. Suitable methods for the use of such cleavage agents are well known in the art. For example, see EP 100,641A.

Particularly advantageous is enzymatic digestion of receptor ligand complexes followed by adsorption of the digest onto immobilized anti-ligand columns and elution or separation of the ligand-bound fragment. This helps to reduce the risk that the cleavage method employed will hydrolyze the receptor in an exposed ligand binding site; in essence, the ligand protects the receptor. The same effect can be achieved by preincubating the receptor with agonist or antagonist antibody obtained as described above, in order to bind the receptor in the key regions. The separation column in this instance will contain immobilized polyclonal anti-agonist or antagonist antibody. Enzymes should be selected for use in the foregoing binding partner digestions that have a minimal effect on the ligand or antibody but which exert maximal cleavage of the receptor. This is readily determined by selecting enzymes and incubation conditions that produce the smallest number of ligand or anti-receptor fragments.

Photoaffinity crosslinking of the receptor active site with labelled ligand or anti-receptor is another technique that can be employed to identify the ligand binding region of the receptor. See K. Muramoto et al., "Biochemistry" 20: 3380 (1981) and H. Bayley, *Photogenerated Reagents in Biochemistry and Molecular Biology* (1983). The polypeptide fragments resulting from digestion of the photocrosslinked receptor-ligand complex are separated on electrophoresis gels or by high pressure liquid chromatography in accordance with conventional practice, the fragment containing the labelled complex recovered, the receptor fragment separated from residual ligand by cleaving the photogenerated bond, and the amino acid sequences determined for the fragment(s) to which the ligand has become attached.

The foregoing methods are helpful in identifying the receptor domain that will provide the best candidates for the desired immunogens. While these fragments alone can be used as immunogens as described below, they are also useful in identifying shorter or flanking sequences that may serve as more precise immunogens. It is convenient to manufacture these sequences by organic synthesis. For example, a bank of 15-residue synthetic fragments could be synthesized based on the sequence of an entire hypothetical 40-residue trypsin fragment of a receptor found to bind to an agonist antibody in competition with ligand. Other fragments are synthesized based on knowledge of the receptor amino acid sequence that includes 5-10 residues amino or carboxy terminal from the hypothetical 40-residue fragment. The receptor fragment size generally will exceed 5 residues.

Suitable methods per se are known for producing polypeptide fragment immunogens where the fragments represent portions of larger proteins. Generally these methods entail linking the receptor fragment or, optionally other receptor derivatives, to a immunogenic carrier protein in the same way as is described above for rendering the intact receptor or anti-ligand antibody (or a segment thereof) immunogenic. The same conjugating methods and immunogenic substances are suitable. However, the candidate polypeptides are rather smaller, i.e., about from 5 to 20 residues, and they accordingly cannot be expected to maintain proper receptor conformation as readily as larger fragments. Thus a library or bank of conjugates will be synthesized in order to increase the probability of obtaining a conjugate effective for the desired autoimmunization.

The bank of conjugates will be prepared as a four-way matrix using the following variables: Polypeptide amino acid sequences (including intact receptor), immunogenic substance (including covalent-derivatizing organic small molecules), conjugating agent (where needed to cross-link the receptor or its fragment to a large molecule) and degree of receptor substitution with the immunogenic substance. The degree of substitution will range about from 10 percent to 90 percent of the available conjugating sites on the receptor polypeptide. If the selected polypeptide sequence as found in the receptor does not contain a residue needed for cross-linking, that residue can be inserted during the synthesis of the sequence. For example, N or C terminal cysteines (or both) are inserted into a selected sequence to facilitate conjugation with sulfhydyl group-containing residues of the immunogenic protein using M-maleimidobenzoyl sulfosuccinimide esters.

The conjugate library then is assayed for the ability of agonist or antagonist antibody to bind one or more of its members. This serves as an initial survey for receptor derivatives (conjugates) most likely to induce the desired immune response, for if a conjugate binds to an antibody having the desired activity the conjugate in turn will be considered a likely candidate to raise such antibodies upon immunization. The immunogenic carrier, if any, used to raise the agonist or antagonist antibody should not be the same as that of the polypeptide conjugate. Otherwise, false positives from anti-immunogenic protein antibodies will occur, at least if the agonist or antagonist antibody is polyclonal. It may be necessary to screen a large number of conjugates in order to locate suitable cross-reacting conjugates, but this will be routine experimentation not involving any independent invention. It is not critical that the immunogenic conjugates be prescreened in this fashion. However, the efficiency of in vivo immunogenicity will be enhanced considerably.

The ability of a conjugate to bind to the antibody in question is determined by permitting the insolubilized agonist or antagonist antibody to bind to conjugate and separating the resulting binding mixture on e.g. native (nondenaturing, nonreducing) polyacrylamide gel electrophoresis. A band representing the complex, visualized by labelled anti-agonist or anti-antagonist species immunoglobulin, will appear in a different position in comparison with the unbound antibody.

Immunogenic receptor derivatives demonstrating at least detectable affinity for the test antibody are used to immunize animals as required for stimulation or inhibition of receptor acitivity. The animal species immunized should be the same species from which the receptor polypeptide was derived, or at least have receptors homologous to that species. Ultimately, successful experiments with immunogens of either embodiment of this invention will produce the desired therapeutic efficacy, e.g. enhanced milk production or inhibition of tumor growth and proliferation. Failure to produce the desired efficacy, however, may result from an absence of proper immunization. Therefore the generation of anti-receptor antibodies in animals having received immunogenic conjugates should be followed by obtaining plasma samples at weekly intervals and assaying the plasma for anti-receptor antibodies, including those having agonist and/or antagonist activity. Booster immunizations should follow the first treatment, particularly if none of the expected antibodies is found within 1 month of the initial immunization attempt. The level of agonist or antagonist antibody is thereafter correlated with the therapeutic effect. This will enable one to schedule booster immunizations to titer the antibody level to the desired therapeutic effect.

The following examples are intended to merely illustrate the best mode now known for practicing the invention, but the invention is not to be considered limited thereto.

All literature citations herein are expressly incorporated by reference.

EXAMPLE 1

Preparation of Neutralizing Antibody to Human or Bovine Growth Hormone (hGH)

N-terminal methionyl hGH or bGH is prepared in recombinant bacterial cell culture following known methods, e.g. EP 111814A. The remainder of this example is concerned with the production of anti-hGH. However, it will be understood that it is equally applicable to the preparation of anti-bGH secreting hybridomas. Balb/c mice are immunized three times with recombinant methGH, each injection consisting of about 20 μg of methGH. The first injection is given subcutaneously in complete Freund's adjuvant followed at 4 week intervals by subcutaneous injections in incomplete Freund's adjuvant. Spleen cells from injected Balb/c mice are fused with P 3×63-Ag8.653 (ATCC CRL 1580) hybrid cells using the polyethylene glycol fusion procedure of T. McKearn et al., "Immunol. Rev." 47: 91 (1979). Hybridoma supernatants are screened for anti-hGH antibody by adsorbing the supernatants onto plastic microtiter wells, rinsing with a 0.1 percent BSA solution in PBS, washing the wells with PBS to remove unadsorbed supernatant and BSA, adding horseradish peroxidase-conjugated methGH, incubating, washing, adding substrate and measuring the amount of absorbance at 492 nm in each well. Monoclonal antibody supernatants from hybridomas of unimmunized, mouse spleen cells are used as a control. The absorbance found in the test wells was directly proportional to the murine anti-hGH antibody.

Monoclonal murine anti-hGH antibody that is capable of neutralizing hGH activity is identified by determining its effect on the activity of growth hormone in known methods for determining growth hormone bioactivity. In these methods dilutions of anti-bGH or anti-hGH monoclonal antibodies are combined with metbGH or methGH, as the case may be, incubated in order to permit binding of the antibodies to the hormones and the bound hormones then assayed for bioactivity. When bioactivity is reduced in inverse proportion to the degree of dilution of the monoclonal antibody it is concluded that the antibody is a neutralizing antibody. If the antibody is non-neutralizing the bioactivity will remain largely unaffected by the amount of antibody that binds to the hormone. In one such method for assaying hGH bioactivity, Tanaka et al., "J. Clin. Endocrin. and Metab." 51(5): 1058-1063 (1980), Nb 2 rat lymph node lymphoma cells are maintained as suspension cultures in 75-cm$^2$ tissue culture flasks (Falcon Plastics, Los Angeles, CA) in Fischer's medium supplemented with horse serum (HS; 10 percent), fetal calf serum (FCS; 10 percent), 2-mercaptoethanol (2-ME; $10^{-4}$M), pencillin (50 U/ml), and streptomycin (50 $\mu$g/ml) in an atmosphere of 5 percent $CO_2$-95 percent air at 37° C. Under these conditions, the cell population doubles in approximately 20 h.

Approximately 24 h before their use in the bioassay, NB 2 cells are transferred to Fischer's medium supplemented with 1 percent FCS, 10 percent HS, $10^{-4}$M 2-ME, and antibiotics and incubated for about 24 h in order to slow down the rate at which the cells replicate. At the end of this period, the cells are collected by centrifugation (3 min at 300×g) and resuspended at a concentration of 1-2×10$^5$ cells/ml in Fischer's medium supplemented with 10 percent HS, $10^{-4}$M 2-ME, and antibiotics. Two-milliliter aliquots are distributed in 35-mm tissue culture dishes (Falcon Plastics). The candidate test samples are prepared by combining a stoichoimetric excess of monoclonal antibody with methGH, generally a molar ratio of greater than ½ mole of antibody for 1 mole of methGH. Since the hybridoma supernatants are not purified and may contain varying amounts of antibody, the test hybridoma supernatant is diluted 1:1, 1:10, 1:100, 1:1000 and 1:10,000 into control hybridoma supernatants. These, as well as neat supernatant, in turn are diluted 1:100 into PBS containing 0.1 percent bovine serum albumin. 50 $\mu$l of each final dilution in PBS is added to 50 $\mu$l of methGH solution and incubated overnight in order to permit immune binding of the methGH. Hybridoma supernatants prepared from unimmunized mice spleen cell fusions are used as controls.

100 $\mu$l of the incubated solution is added to the 2 ml cultures. The cultures are incubated in a $CO_2$ incubator for 72 h at 37° C., and the cell numbers then determined using a Coulter counter (Coulter Electronics, Inc., Hialea, FL). All samples are assayed in duplicate. Growth in control cultures is essentially zero over the 3-day incubation period. A clone is identified by this method that secretes an antibody that progressively inhibits stimulation of Nb 2 growth by methGH as the degree of dilution is decreased, i.e., Nb 2 cell growth is more inhibited with neat supernatant than with supernatant diluted to 1:10,000.

In an alternative method, the effect of the candidate antibody on rat weight gain is determined. This method is used in evaluating bGH as well as hGH neutralizing antibodies. Hypophysectomized albino "CD" female rats (Charles River Laboratory) are weighed every 2-3 days for at least 10 days prior to starting injections. Any animal with a weight fluctuation of 7 g or more or an absolute weight outside the range 85-110 g is excluded from the study.

The standard and each test lot are given at two doses, 10 and 50 ug/day. Eight or more animals are assigned to each treatment group so that the mean body weights for the groups are approximately equal prior to treatment. Animals are caged so treatment groups are balanced in the cages to eliminate bias resulting from housing.

Standard methGH (2.0 International Units/mg) is diluted or reconstituted to 1 mg/ml. This solution is further diluted into 1:100 PBS dilutions of candidate hybridoma supernatant dilutions in control supernatant according to the Table 2 below:

TABLE 2

| Final mhGH Concentration | Buffer Sample Volume (dilutions of immune supernatant by non-immune supernatant) | Growth Hormone Solution (1 mg/mL) |
| --- | --- | --- |
| 500 $\mu$g/ml | 7.5 ml (0:1) | 7.5 ml |
| 500 $\mu$g/ml | 7.5 ml (1:10) | 7.5 ml |
| 500 $\mu$g/ml | 7.5 ml (1:100) | 7.5 ml |
| 500 $\mu$g/ml | 7.5 ml (1:1000) | 7.5 ml |
| 500 $\mu$g/ml | 7.5 ml (1:10,000) | 7.5 ml |
| 100 $\mu$g | 13.5 ml (0:1) | 1.5 ml |
| 100 $\mu$g | 13.5 ml (1:10) | 1.5 ml |
| 100 $\mu$g | 13.5 ml (1:100) | 1.5 ml |
| 100 $\mu$g | 13.5 ml (1:1000) | 1.5 ml |
| 100 $\mu$g | 15.5 ml (1:10,000) | 1.5 ml |

The test solutions should contain approximately the same protein content by Lowry assay. The test solutions are stored at 2°-8° C. for a period sufficient to permit the monoclonal antibody to bind the methGH, generally overnight.

Following construction of animal test groups as described above, rats are injected with 0.1 mL of test solutions (equivalent to 10 and 50 ug) subcutaneously in the abdominal-inguinal region for ten consecutive days. Whole body weights are determined (to the nearest gram) immediately prior to injection on each day of injection and on the day following the last injection. Weights are determined and injections are given at approximately the same time each day.

The specific activity of the test samples is computed by multiplying the specific activity of the reference material by the relative potency of the test sample. The relative potency of the test sample and its 95 percent confidence interval are computed using the formulas of Bliss "Biometrics" 12: 491-526 (1956). Response is fit to the logarithm of dose for a standard preparation and a test preparation. The slopes of these fits are constrained to be equal. The log relative potency is a/b where b is the common slope and a is the difference of the intercepts of the two lines. The 9.5 percent confidence limits are computed in accord with known methods using the algorithm.

$x_m' =$

-continued $$\frac{ab - v_{ab}t^2}{b^2 - v_{bb}t^2} \pm \left[ \frac{(ab - v_{ab}t^2)^2 - (a^2 - v_{aa}t^2)(b^2 - v_{bb}t^2)}{(b^2 - v_{bb}t^2)^2} \right]^{\frac{1}{2}}$$

The relative potency and its 95 percent confidence limits are obtained by exponentiating the log relative potency and its confidence limits.

A clone is identified by this method which secretes antibody that progressively inhibits the stimulation of rat growth by methGH as the degree of supernatant dilution is decreased. This method is used in identical fashion to assay the ability of anti-bGH (bovine growth hormone) synthesizing hybridomas obtained as described above for hGH to neutralize bGH growth promoting activity in rats.

EXAMPLE 2

Immunization of Cattle and Sheep with Murine Anti-hGH or Anti-bGH Neutralizing Antibody Neutralizing monoclonal antibodies produced in Example 1 are purified from culture supernatant using ammonium sulfate precipitation followed by ion-exchange or protein A affinity chromatography (Livingston, D. M., 1974, "Methods in Enzymol." 34: 725). 0.1–1.0 mg of purified antibody or antibody coupled to KLH or STI with glutaraldehyde in 1 ml of PBS is emulsified with 1 ml of Freund's adjuvant. The initial injection is emulsified with Complete Freund's adjuvant and subsequent injections contain Incomplete Freund's adjuvant. Alternatively, the antibody is precipitated with aluminum hydroxide (Sanchez et al., 1980, "Infect. Immun.", 30: 728–733) and injected as a suspension of antibody and adjuvant in 2 ml of PBS. An alternative immunization scheme uses $5 = 10^6$ irradiated hybridoma cells suspended in 2 ml of PBS. Sheep and lactating dairy cattle are injected at 0, 4 and 8 weeks with 0.5 ml of cell or antibody preparations in 4 subcutaneous sites. The animals are bled weekly and the serum globulin fraction is tested for bGH agonist activity in the rat growth and Nb 2 assays described in Example 1. The daily lactation of the cattle is measured daily and animal weights of sheep and cattle are monitored periodically. One of the neutralizing antibodies of Example 1 consistently produced an agonist immune response in the cattle that significantly enhanced milk production and another consistently produced significant weight gains in sheep.

EXAMPLE 3

Preparation of Immunogens for Raising EGF Agonist Antibody

A human EGF receptor agonist murine monoclonal antibody is produced using the method of A. Schreiber et al., op cit. This antibody is designated AAb1. Polypeptides corresponding to the EGF receptor amino acid residues described in Table 2 below were synthesized by the technique described in R. Merrifield, "J. Am. Chem. Soc." 85: 2149–2154 (1963). These residues represent sequences N-terminal from the EGF receptor transmembrane domain and at least one of which is suspected to contain at least a portion of the EGF binding site. The completed polypeptides were separated from the resin and partially purified by gel filtration on G-15 (Sephadex). Sequences were confirmed by gas phase sequencing. In Table 3 KLH means keyhole limpet hemocyanin while STI means soybean trypsin inhibitor.

TABLE 3

| Cross-linking Agent | EGFR Polypeptide | Protein |
|---|---|---|
| MBS[a] | 120–133 | KLH |
| MBS | 133–147 | KLH |
| MBS | 149–163 | KLH |
| MBS | 240–255 | STI |
| MBS | 250–267 | STI |
| MBS | 261–269 | STI |
| MBS | 240–267 | STI |
| MBS | 260–270 | STI |
| MBS | 268–282 | STI |
| MBS | 272–282 | KLH |
| MBS | 280–293 | KLH |
| MBS | 303–315 | KLH |
| MBS | 338–354 | STI |
| MBS | $Cys^{(365)}$ 366–381[c] | STI |
| MBS | 446–462 | STI |
| MBS | $Cys^{(423)}$ 424–444[c] | STI |
| MBS | 464–475 | STI |
| NHS[b] | 91–106 | KLH |
| NHS | 109–124 | KLH |
| NHS | 155–165 | STI |
| NHS | 237–246 | STI |
| NHS | 250–260 | STI |
| NHS | 260–269 | STI |
| NHS | 270–282 | STI |
| NHS | 285–307 | STI |
| NHS | 311–321 | STI |
| NHS | 314–327 | STI |
| NHS | 358–372 | KLH |
| NHS | 375–387 | KLH |
| NHS | 392–407 | KLH |
| NHS | 407–419 | KLH |
| NHS | 430–442 | KLH |
| NHS | 476–491 | KLH |
| NHS | $lys^{(482)}$ 483–500[c] | KLH |
| NHS | 514–532 | KLH |
| NHS | 585–587 | KLH |

[a]MBS: m-Maleimidobenzoyl sulfosuccinimide ester. Conjugation is through cysteine residues.
[b]NHS: N—hydroxysuccinimide. Conjugation is through lysine residues.
[c]The indicated polypeptide is synthesized with an added N—terminal cysteine or lysine, as shown.

Candidate immunogens from Table 2 were assayed for the ability to bind antibody AAb1 by the following method. Radioiodinated EGF and varying dilutions of the candidate immunogens are incubated overnight in polystyrene test tubes previously coated with AAb1 and KLH (for KLH immunogens) or STI (for STI immunogens). The test tubes are washed with PBS and counted for bound radioactivity. Candidate immunogens showing the ability to competitively inhibit EGF binding to AAb1 were selected for further study.

1 μg of AAb1 cross-reactive immunogens are emulsified with complete Freund's adjuvant and injected intraperitoneally into mice. The animals are boosted two and four weeks later with the same amount of immunogen in incomplete Freund's adjuvant, given by intraperitoneal injection. Six weeks after the initial immunization the animals are bled and antisera recovered by ammonium sulfate precipitation of the murine IgG fraction and resolubilization in PBS. Antisera are identified that act as EGF agonists in the in vitro cell assay described by A. Schreiber et al., op cit.

EXAMPLE 4

The amino acid and nucleotide sequences for the human and rabbit growth hormone receptors are set forth in FIGS. 1 and 2. growth hormone receptors from other animals are readily obtained by using labelled nucleotide fragments from the FIGS. 1 and 2 sequences to probe for homologous sequences in genomic or liver mRNA libraries from other animal species. The relevant portions of these sequences for the purposes of this invention are the extracellular domains extending from residue 1 to about 247. Agonist or antagonist immunogens are identified by preparing fragments of these receptor domains having about from 10 to 20 residues each. One set of fragments will commence at residue 1 and procede in increments of about the same size (10–20 residues) through the entire extracellular domain (for a total of about 12 to 24 fragments). Another set will commence at about residue 5 and procede in increments of about the same size to about residue 247. Accordingly, a total screen of about 24 to 48 fragments will be linked to polypeptides or haptens in order to prepare immunogens an their activity evaluated in the target animal species as described above.

If the desired immunogen is not obtained at this point, and in the case of the growth hormone receptor the desired immunogen preferably will produce a consistent agonist response in the target species, then further steps will be taken. First, the method for linking the immunogenic polypeptide to the fragments is modified so as to change the residue on the fragment which is linked to the immunogen, e.g., by preparing the fragment with an N- or C-terminal cysteine or tyrosine for cross-linking to the immunogenic carrier, by changing the cross-linking agent (for example so that the carrier is linked through a primary amino group rather than a carboxyl side chain of the fragment; see Table 1 above or Erlanger in Vunakis et al., "Methods in Enzymology" 70: 85–105 [1980]), or by synthesizing the fragment in recombinant cell culture as an N- or C-terminal fusion with the immunogen. N-terminal fusions also can be produced by succinylating the carrier polypeptide, leaving only the N-terminal amine for activation with carbodiimide and cross-linking to the receptor fragment or its N- or C-terminal tyrosinyl or cysteinyl analogue. Conjugates at the N- or C-terminal ends of the carrier polypeptide are advantageous over conjugates in which the fragment is cross-linked to an internal functionality of the carrier because the former can be reproducibly synthesized and therefore may result in a more consistent immune response.

Particularly interesting domains of the growth hormone receptor extracellular domain will be regions in which the hydropathy (as determined by the method of Kyte et al., "J. Mol. Biol." 153: 105–132 [1982]) is from about 0 to −2.5. For example (refering to the human sequence shown in FIG. 2), the growth hormone receptor sequences about from 13–99, 119–131, 150–187, and 200–230 would be useful candidates.

Other derivatives of the growth hormone receptor extracellular domain are prepared from the intact approx. 247 residue sequence, rather than employing fragments thereof. The intact sequence is cross-linked to immunogenic carriers or to haptens in the same fashion as are the fragments. Particularly interesting results are obtained by cross-linking haptens such as dinitrophenol through various classes of amino acid side chains, such as hydroxyl, amino or carboxyl, which are present on the intact extracellular domain. An animal population is immunized with these preparations and the immune response evaluated.

The cloning and expression in recombinant cell culture of the growth hormone receptor or its extracellular domain are further described in U.S. Pat. Ser. No. 62,542, filed of even date and which is hereby expressly incorporated by reference.

We claim:

1. A method for immunizing an animal against its growth hormone receptor comprising vaccinating the animal against a growth hormone receptor extracellular domain derivative, said derivative having been predetermined to raise polyclonal antisera in a predetermined animal species which affect the receptor as a growth hormone agonist.

2. The method of claim 1 wherein the derivative is a growth hormone receptor fragment covalently linked to an immunogenic carrier substance.

3. The method of claim 2 wherein the immunogenic carrier substance is a protein foreign to the animal to be immunized.

4. The method of claim 1 wherein the fragment is greater than about 5 residues.

5. The method of claim 2 wherein the receptor fragment is homologous with the growth hormone receptor of the animal to be immunized.

6. A growth hormone receptor extracellular domain derivative predetermined to raise polyclonal antisera in a predetermined animal species which polyclonal antisera bind to the receptor as a growth hormone agonist.

7. The derivative of claim 6 which is a conjugate of a growth hormone receptor polypeptide fragment and an immunogenic carrier protein.

8. The derivative of claim 1 wherein the animal is a human, bovine, porcine or ovine.

9. The method of claim 1 wherein the growth hormone receptor is a product of recombinant cell culture.

10. The derivative of claim 6 wherein the growth hormone receptor is a product of recombinant cell culture.

* * * * *